United States Patent [19]
Balzar

[11] Patent Number: 5,873,971
[45] Date of Patent: Feb. 23, 1999

[54] METHOD OF FORMING A TAMPON WHICH CAN BE COMFORTABLY WITHDRAWN FROM A BODY CAVITY

[75] Inventor: Tammy Jo Balzar, Menasha, Wis.

[73] Assignee: Kimberly Clark Worldwide, Inc., Neenah, Wis.

[21] Appl. No.: 749,127

[22] Filed: Nov. 14, 1996

[51] Int. Cl.⁶ ..................................................... A61F 13/22
[52] U.S. Cl. ........................... 156/217; 28/120; 156/227; 604/904; D24/141
[58] Field of Search ..................................... 156/212, 213, 156/217, 218, 227; 28/120, 118; 424/431; 604/904; D24/141

[56] References Cited

U.S. PATENT DOCUMENTS

| | | | |
|---|---|---|---|
| 2,092,427 | 9/1937 | Ross | 604/364 |
| 2,264,586 | 12/1941 | Ross | 604/15 |
| 2,487,200 | 11/1949 | Trager | 604/385.1 |
| 2,501,972 | 3/1950 | Seidler | 604/15 |
| 2,711,173 | 6/1955 | Seidler | 604/15 |
| 2,938,519 | 5/1960 | Marco | 128/887 |
| 3,138,159 | 6/1964 | Schmidt | 604/385.1 |
| 3,369,544 | 2/1968 | Crockford | 604/15 |
| 3,643,661 | 2/1972 | Crockford | 604/15 |
| 3,706,311 | 12/1972 | Kokx et al. | 604/15 |
| 3,749,094 | 7/1973 | Duncan | 604/15 |
| 3,762,413 | 10/1973 | Hanke | 604/15 |
| 4,212,301 | 7/1980 | Johnson | 604/385.1 |
| 4,266,546 | 5/1981 | Roland et al. | 604/365 |
| 4,335,721 | 6/1982 | Matthews | 604/363 |
| 4,486,191 | 12/1984 | Jacob | 604/330 |
| 5,084,038 | 1/1992 | Sheldon et al. | 156/193 X |
| 5,112,348 | 5/1992 | Glassman | 604/358 |
| 5,158,535 | 10/1992 | Paul et al. | 604/15 |
| 5,273,521 | 12/1993 | Peiler et al. | 604/13 |
| 5,533,990 | 7/1996 | Yeo | 604/363 |
| 5,659,934 | 8/1997 | Jessup et al. | 28/120 |

Primary Examiner—Francis J. Lorin
Attorney, Agent, or Firm—Thomas J. Connelly; Douglas G. Glantz; Douglas L. Miller

[57] ABSTRACT

A method is disclosed of forming a tampon is which can be comfortably withdrawn from a body cavity. The method includes the steps of cutting an individual absorbent member from an absorbent strip. Each absorbent member is then shaped to form an elongated absorbent having an outer periphery. A liquid-permeable cover is secured to the outer periphery of the elongated absorbent to form a softwind. The softwind has a first end and a second end and is folded on itself such that the first and second ends are aligned adjacent to one another. The softwind contains two folds therebetween which divide the softwind into first, second and third portions. A withdrawal string is secured to the second portion of the softwind and then the softwind is compressed into a cylindrically shaped pledget. The pledget has an insertion end and a trailing end and the insertion end located adjacent to the second portion. The compressed pledget and attached withdrawal string form a tampon wherein the insertion end is capable of collapsing upon itself as pressure is exerted on the withdrawal string to provide a comfortable removal from the body cavity.

20 Claims, 8 Drawing Sheets

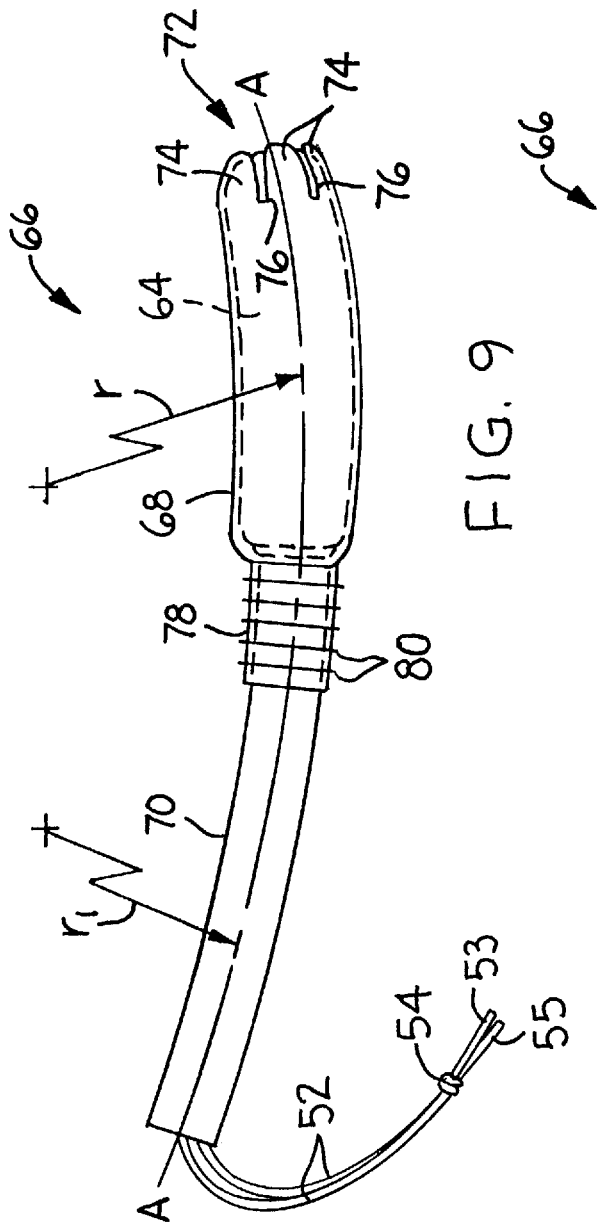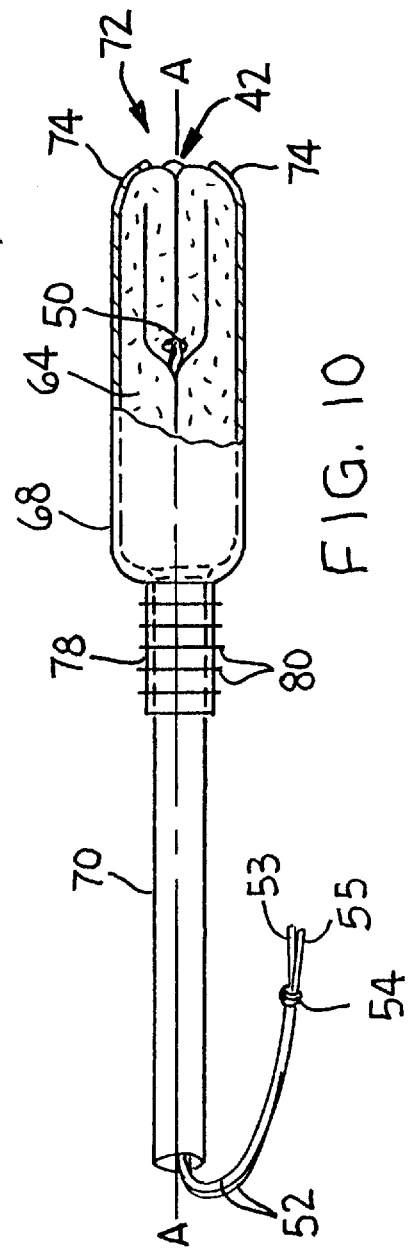

METHOD OF FORMING A TAMPON WHICH CAN BE COMFORTABLY WITHDRAWN FROM A BODY CAVITY

FIELD OF THE INVENTION

This invention relates to a method of forming a tampon which can be comfortably withdrawn from a body cavity. More specifically, this invention relates to a method of forming a tampon having an insertion end which is capable of collapsing upon itself during withdrawal from a body cavity.

BACKGROUND OF THE INVENTION

Currently, there are two basic types of catamenial tampons used for feminine hygiene. The first type is a digital tampon which is designed to be inserted into a woman's vagina directly by the user's fingers. The second type is a tampon which is designed to be inserted with the aid of an applicator. Both types are usually made by folding or rolling a loosely associated strip of absorbent material into an elongated shape referred to as a "softwind". The softwind may or may not include a cover. The softwind is then radially and/or biaxially compressed into a pledget. In both types of tampons, a withdrawal string is attached to the absorbent, either before or after compression, to facilitate removal of the tampon from the user's vagina after it has absorbed a certain quantity of body fluid, such as menses, blood, etc.

It is known that most tampons expand as they absorb body fluid and this larger size and/or diameter can contribute to an uncomfortable withdrawal from the body cavity. In addition, some tampons are designed to mechanically expand once positioned within a body cavity so as to reduce the chance of fluid leakage. This expanded configuration can also contribute to an uncomfortable withdrawal. Tampon users like to use tampons which are comfortable to remove.

Now a method of forming a catamenial tampon has been invented which can be comfortably withdrawn from a body cavity. This tampon has the withdrawal string attached in such a manner that it will cause the insertion end to collapse upon itself such that it is easier to remove from the body cavity.

SUMMARY OF THE INVENTION

Briefly, this invention relates to a method of forming a tampon which can be comfortably withdrawn from a body cavity. The method includes the steps of cutting an individual absorbent member from an absorbent strip. Each absorbent member is then shaped to form an elongated absorbent having an outer periphery. A liquid-permeable cover is secured to the outer periphery of the elongated absorbent to form a softwind. The softwind has a first end and a second end and is folded on itself such that the first and second ends are aligned adjacent to one another. The softwind contains two folds therebetween which divide the softwind into first, second and third portions. A withdrawal string is secured to the second portion of the softwind and then the softwind is compressed into a cylindrically shaped pledget. The pledget has an insertion end and a trailing end with the insertion end located adjacent to the second portion. The compressed pledget and attached withdrawal string form a tampon wherein the insertion end is capable of collapsing upon itself as downward pressure is exerted on the withdrawal string to provide a comfortable removal from the body cavity.

The general object of this invention is to provide a method of forming a catamenial tampon which can be comfortably removed from a body cavity. A more specific object of this invention is to provide a method of forming a tampon which has an insertion end which is capable of collapsing upon itself to provide for a comfortable removal from a woman's vagina.

Another object of this invention is to provide an efficient method of forming a catamenial tampon.

A further object of this invention is to provide a method of forming a tampon having a generally M-shaped profile having more absorbent material located at the insertion end than at the trailing end so as to reduce the possibility of fluid leakage during use.

Still another object of this invention is to provide a method of forming a tampon which is easy to perform and economical.

Still further, an object of this invention is to provide a method of forming a tampon which can expand upon insertion into a body cavity and collapse to a smaller size and/or diameter during the removal process.

Other objects and advantages of the present invention will become more apparent to those skilled in the art in view of the following description and the accompanying drawings.

BRIEF DESCRIPTION OF THE DRAWINGS

FIG. 9 is a side view of a two piece, arcuately shaped tampon applicator having an inner tube and an outer tube.

FIG. 10 is a cross-sectional view of the tampon applicator shown in FIG. 9, rotated 90° and partially broken away to show the orientation of the tampon relative to the curvature of the outer tube prior to insertion of the tampon into a woman's vagina.

DETAILED DESCRIPTION OF THE PREFERRED EMBODIMENTS

Figure 1:
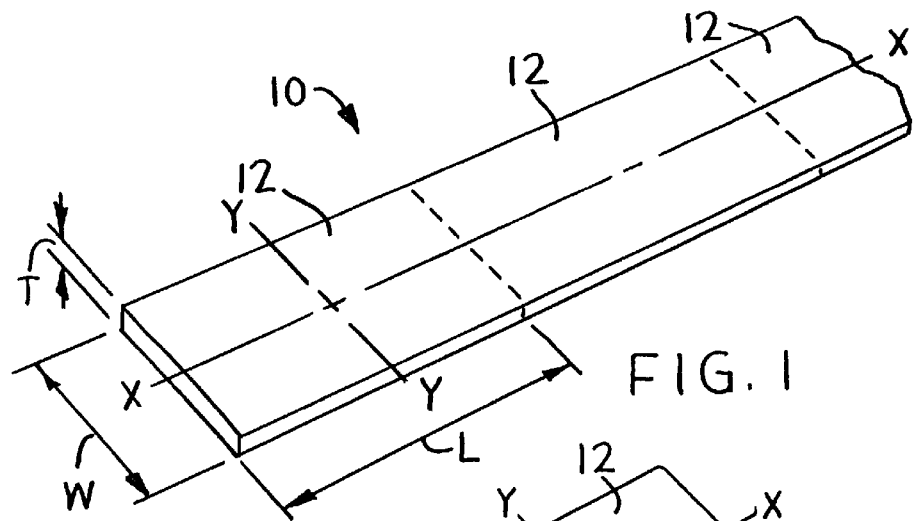
FIG. 1 is a perspective view of an elongated ribbon of absorbent material which can be cut into individual segments.

Referring to FIG. 1, an elongated absorbent ribbon 10 is shown which can be cut into two or more individual members 12. Each of the individual members 12 can be in the form of a rectangle having a length L, a width W and a thickness T. Preferably, the length L will be greater than the width W and the width W will be greater than the thickness T.

The absorbent ribbon 10 can be formed from absorbent fibers which are assembled into a sheet or ribbon. Alternatively, the absorbent fibers can be assembled and formed into a generally cylindrical configuration, if desired. The absorbent ribbon 10 can be formed from cellulosic fibers, such as cotton and/or rayon. The absorbent fibers can be 100% cotton, 100% rayon, or a blend of cotton and rayon fibers. Some blends which have been tried and work well include a blend of about 15% cotton to about 85% rayon; about 70% cotton to about 30% rayon; about 60% cotton to about 40% rayon; about 25% cotton to about 75% rayon; and about 6% cotton to about 94% rayon. The particular blend of fibers can vary depending upon preference. It is also possible to add polyester or other synthetic fibers to the blend to add resilient features to the absorbent 10.

When cotton fibers are used, the cotton fibers should have a staple length of between about 5 millimeters (mm) to about 20 mm. The cotton fibers should generally have a fiber size of between about 150 microns to about 280 microns. The cotton fibers can also be bleached if desired. Bleaching will make the cotton fibers whiter in appearance.

When rayon fibers are present, the rayon fibers should have a staple length of between about 20 mm to about 35 mm. The rayon fibers should have a denier of between about 2 to about 6. As defined by the "Dictionary of Fiber & Textile Technology" which is available from Hoechst Celanese Corporation having a mailing address of P.O. Box 32414, Charlotte, N.C. 28232 on page 42, denier is:

"the unit of fineness of yarn based on a standard of 50 milligrams (mg) for 450 meters of yarn. This is numerically equal to the weight in grams of 9,000 meters of the material. Denier is a direct numbering system in which the lower numbers represent the finer sizes and the higher numbers the coarser sizes."

The rayon fibers can have a circular cross-sectional configuration, a bi-lobal cross-sectional configuration, a tri-lobal cross-sectional configuration, or some other cross-sectional configuration known to those skilled in the art. The bi-lobal configuration has a cross-sectional profile which looks like a dogbone while the tri-lobal configuration has a cross-sectional profile which looks like a "Y". The rayon fibers can also be bleached if desired.

The absorbent 10, when formed from an absorbent sheet or ribbon, can be constructed from a blend of cotton and/or rayon fibers. Two processes for forming such an absorbent sheet are known as "carding" and "airlaying." Depending upon the desired absorbency one desires in the finished tampon, the basis weight of the absorbent ribbon can vary. The U.S. Food and Drug Administration (FDA) has set absorbency standards for "junior", "regular", "super" and "super-plus" size tampons. In order to meet the FDA standards for the four sizes, the absorbent sheets 10 are targeted to have basis weights of about 100 grams per square meter (gsm), 120 gsm, 170 gsm and 230 gsm, respectively. Typically, the carding process is controlled to produce an absorbent ribbon 10 having a width W of between about 40 mm to about 60 mm, preferably about 50 mm. The basis weight and/or the length of the absorbent can also be adjusted to form the different size tampons.

The length L of the individual absorbent member 12 can vary from between about 100 mm to about 200 mm. For the "regular" size tampon, a length L of between about 140 mm to about 150 mm is sufficient.

In FIG. 1, each of the individual absorbent members 12 will have a central longitudinal axis X—X, which is in the machine direction, and a central transverse axis Y—Y, which is aligned perpendicular to the axis X—X. The central longitudinal axis X—X will be used as a reference line in some of the following figures in order to describe forming the absorbent ribbon 10 into a tampon.

Figure 2:
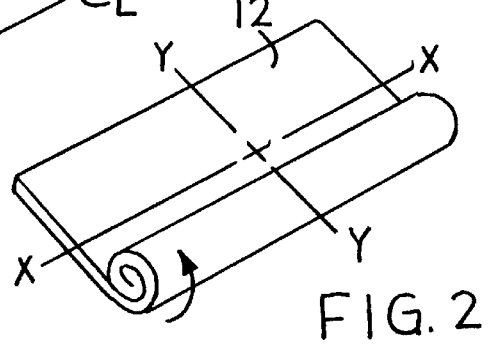
FIG. 2 is a perspective view of an individual absorbent segment being rolled up into a cylindrical profile.
Figure 3:
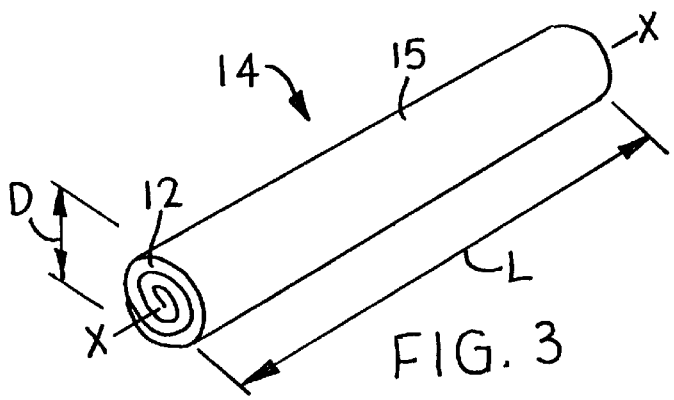
FIG. 3 is a perspective view of the individual absorbent segment having been rolled up into an elongated cylindrical shape.

Referring to FIGS. 2 and 3, an individual absorbent member 12 is shown which is rolled or folded along the central transverse axis Y—Y to form a generally elongated absorbent 14, see FIG. 3. The elongated absorbent 14 can have a cylindrical shape, a rectangular shape, an oval shape, a square shape, etc. Preferably, the elongated absorbent 14 will have a cylindrical shape with a circular cross-section. The cross-section can have a diameter D, see FIG. 3, which is between about 10 mm to about 20 mm. Preferably, the diameter D will be between about 12 mm to about 15 mm. The actual diameter D of the elongated absorbent 14 can vary depending upon whether it is going to be used to make a "junior", "regular", "super" or "super-plus" size tampon. The length of the elongated absorbent 14 will be approximately equal to the length of the starting individual member 12.

Figure 4:
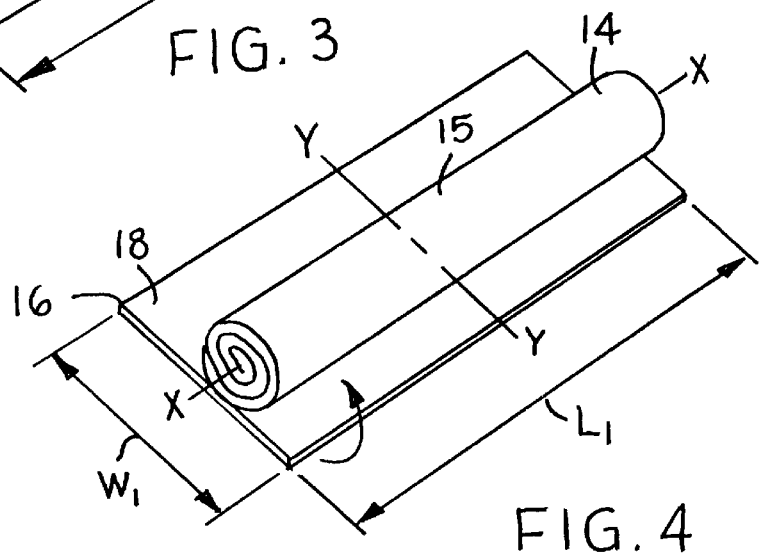
FIG. 4 is a perspective view of the elongated cylindrically shaped absorbent positioned on a rectangular sheet of cover material.
Figure 5:
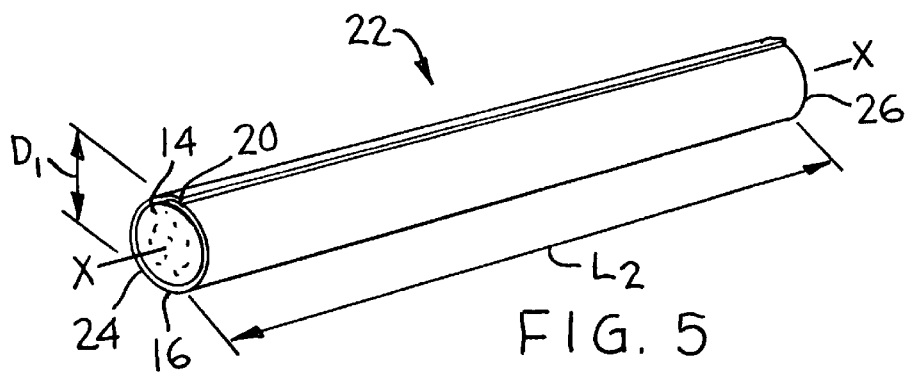
FIG. 5 is a perspective view of the absorbent rolled up with the cover material to form a "softwind."

Referring now to FIGS. 4 and 5, the elongated absorbent 14 is placed or positioned on a liquid-permeable cover 16. The cover 16 will have a first major surface 18 and can be formed as a rectangular sheet, as shown. The cover 16 has a length L, and a width $W_1$ which are sized so that the cover 16 can wrap completely around the outer periphery of the elongated absorbent 14. Preferably, the cover 16 will have a length L, which is equal to or greater than the length L of the elongated absorbent 14 and will have a width $W_1$ which is greater than the outside periphery of the rolled absorbent 14. By so sizing the width $W_1$ of the cover 16, the cover 16 will be able to wrap completely around the outer exterior surface of the absorbent 14 and be overlapped upon itself at 20, see FIG. 5.

The liquid-permeable cover 16 can be bonded along the entire length of the overlap area 20 by using an impulse sealer or some other type of sealing mechanism. Alternatively, the cover 16 can be spot bonded at spaced apart points along the overlap area 20, if desired. The cover 16 can be bonded to either itself and/or to the absorbent 14 using heat, pressure, heat and pressure, ultrasonics, adhesives, glue, or any other known bonding technique or a combination of two or more of such bonding techniques.

The liquid-permeable cover 16 can be formed from woven or nonwoven material having a porous substrate. Woven material includes textile fabrics which can be made from rayon, cotton, polyolefins or other synthetic yarns. The synthetics can be either staple or continuous filaments. The cover 16 can be a 0.6 ounces per square yard of polypropylene spunbond. The nonwoven materials can include spunbond, bonded carded webs and hydroentangled webs. Spunbond and bonded carded webs are commercially sold by Kimberly-Clark Corporation having an office located at 401 North Lake Street, Neenah, Wis. 54956. Another nonwoven material which can be used as the cover 16 is formed from 100 percent polyester fibers held together by a binder. This material is known as powder-bonded-carded web (PBCW). PBCW is commercially available from HDK Industries, Inc. having an office at 304 Arcadia Drive, Greenville, S.C. 29609. The cover 16 can further be formed from an apertured thermoplastic film having either a two-dimensional or a three-dimensional thickness. Apertured thermoplastic films are available from several commercial vendors including Pantex Sri, Pantex Sud srl, Via Terracini snc. having an office at 51031 Agliana, Pistoia, Italy and Applied Extrusion Technology having a mailing address of P.O. Box 582, Middleton, Del. 19709.

The liquid-permeable cover 16 can be treated with an aqueous solution to reduce frictional drag, to enhance the tampon's wettability and to enhance the ease of insertion into and withdrawal from a woman's vagina. The cover 16 can be treated either before being rolled or folded up with the absorbent ribbon 10 or after the cover 16 has been positioned about the exterior surface of the elongated absorbent 14. The different types of aqueous solutions which can be used are known to those skilled in the art. One particular type of aqueous solution is taught in U.S. Ser. No. 08/311,692, filed Sep. 23, 1994 and entitled "TAMPON EXHIBITING LOW FRICTIONAL DRAG". This patent application is assigned to Kimberly-Clark Corporation and is incorporated by reference and made a part hereof.

Referring again to FIG. 5, the absorbent ribbon 10 and the liquid-permeable cover 16 are rolled into a generally cylindrical-shape known as a "softwind" 22. The softwind 22 has a central longitudinal axis X—X and is an elongated member. The softwind 22 can have a shape different from the cylindrical shape if desired. The softwind 22 has a first end 24 and a second end 26. The first and second ends, 24 and 26 respectively, are spaced apart from one another. The softwind 22 can have a length $L_2$ of up to about 10 inches (about 254 mm). Preferably, the softwind 22 has a length $L_2$ of from between about 2 inches to about 8 inches (about 50 mm to about 203 mm), and most preferably, it has a length $L_2$ of about 6 inches (about 152 mm). When the softwind 22 has a circular cross-sectional configuration, it can have a diameter $D_1$ ranging from between about 0.5 inches (about 13 mm) to about 2 inches (about 50 mm), and preferably, will have a diameter $D_1$ of about 1 inch (about 25.4 mm). The specific diameter $D_1$ of the softwind 22 will be dictated by the type of tampon which is to be formed, such as a "junior", "regular", "super", or "super-plus" size. The softwind 22 is generally not compressed but if compressed, is not compressed a substantial amount.

Figure 6:
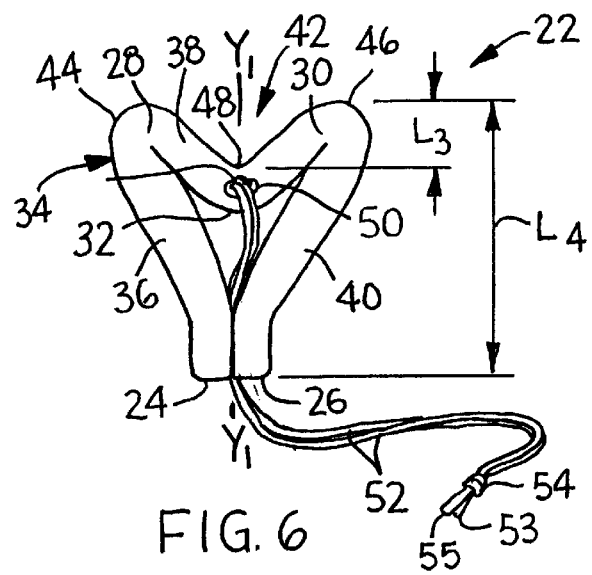
FIG. 6 is a side view of the softwind folded to form a generally M-shaped profile and having an aperture formed through the second portion which receives a withdrawal string.

Referring to FIG. 6, the softwind 22 is folded or bent upon itself such that the first and second ends, 24 and 26 respectively, are aligned adjacent to one another. The softwind 22 contains at least two and preferably three folds 28, 30 and 32 located between the ends 24 and 26. The three folds 28, 30 and 32 configure the softwind 22 into a generally M-shaped profile 34 with the first and second ends, 24 and 26 respectively, forming the base of the M-shaped profile 34. In the M-shaped profile 34, the softwind 22 is folded at 28 to form a first portion 36 and is folded at 30 to form a second portion 38 and a third portion 40. The first, second and third portions, 36, 38 and 40 respectively, can have approximately the same length. For example, if the softwind 22 has a length $L_2$ of about 6 inches (about 150 mm), each of the first, second and third portions 36, 38 and 40 respectively, can have a length of approximately two inches (about 50 mm). Alternatively, the first and third portions, 36 and 40 respectively, can have approximately the same length and the second portion 38 can be smaller or larger than either of the other two portions, 36 and 40 respectively. For example, if the softwind 22 has a length of about 6 inches (about 150 mm), the first and third portions, 36 and 40 respectively, can have a length of about 1.5 inches (about 37 mm) and the second portion 38 can have a length of about 3 inches (about 75 mm).

The softwind 22 is split along the vertically oriented $Y_1$—$Y_1$ axis. The third fold 32 gives the softwind 22 the generally M-shaped profile 34 and also creates a cleft 42 which is spaced an equal distance between a first lobe 44 and a second lobe 46. The first and second lobes, 44 and 46 respectively, are created by the folds 28 and 30. The cleft 42 has a bottom surface or trough 48 which is aligned along the vertical axis $Y_1$—$Y_1$. The depth of the cleft 42 has a dimension $L_3$ while the M-shaped profile 34 has an overall length $L_4$. The length $L_4$ is the vertical dimension of the M-shaped profile 34 measured along the $Y_1$—$Y_1$ axis, between the tip of one of the lobes 44 or 46 and a line drawn parallel through the base formed by the first and second ends 24 and 26. The length $L_3$ of the cleft 42 represents from between about 5% to about 80% of the length $L_4$, preferably, at least about 10% of the length of $L_4$, and most preferably, from between about 15% to about 50% of the length of $L_4$. It has been found that by forming the cleft 42 to a depth $L_3$, which falls between about 5% to about 80% of the total of the length $L_4$ of the M-shaped profile 34, that a tampon can be formed which will span across the width of a woman's vaginal cavity.

The second portion 38 of the softwind 22 contains an aperture 50 formed therethrough and aligned adjacent to the location of the cleft 42. The aperture 50 can be oriented approximately 90° relative to the vertical axis $Y_1$—$Y_1$ and should be formed about half way along the height of the second portion 38. Alternatively, the aperture 50 could be formed closer to the top or bottom surface of the second portion 38, if desired. By forming the aperture 50 half way along the height of the second portion 38, one can be assured that the softwind 22 will be less likely to tear at this point.

A withdrawal string 52 is passed through the aperture 50 and looped upon itself so as to form a secure attachment to the second portion 38. The withdrawal string 52 has two free ends 53 and 55 which can be tied together to form a knot 54. The knot 54 can be located adjacent to the free ends, 53 and 55 respectively, or can be spaced a distance away from the free ends 53 and 55. The knot 54 assures that the withdrawal string 52 will not separate from the second portion 38 of the softwind 22. It should be noted that the withdrawal string 52 should be aligned between the first and second ends 24 and 26 of the softwind 22 and be in direct contact therewith. Alternatively, the withdrawal string 52 can be looped around the outside of the first and second ends, 24 and 26 respectively, thereby eliminating the need to form the aperture 50. The withdrawal string 52 will provide a means for removing the soiled tampon from a body cavity, for example, a woman's vagina.

The withdrawal string 52 can be constructed from various types of threads or ribbons. A thread or ribbon made from 100% cotton fibers works well. The withdrawal string 52 should have a length which extends outward from the softwind 22 a distance of from between about 2 inches to about 8 inches (about 50.8 mm to about 203.2 mm), preferably, from between about 4 inches to about 6 inches (about 102 mm to about 152.4 mm), and most preferably, about 5 inches (about 127 mm). The withdrawal string 52 can be dyed and/or treated with an anti-wicking agent, such as wax, before being secured to the softwind 22. The use of an anti-wicking agent will prevent any body fluids, such as menses or blood, from wicking along the withdrawal string 52 and contacting the inner surface of a woman's undergarment. A dry, clean withdrawal string 52 is preferred by the user, especially when she goes to remove the tampon from her vagina.

Figure 7:
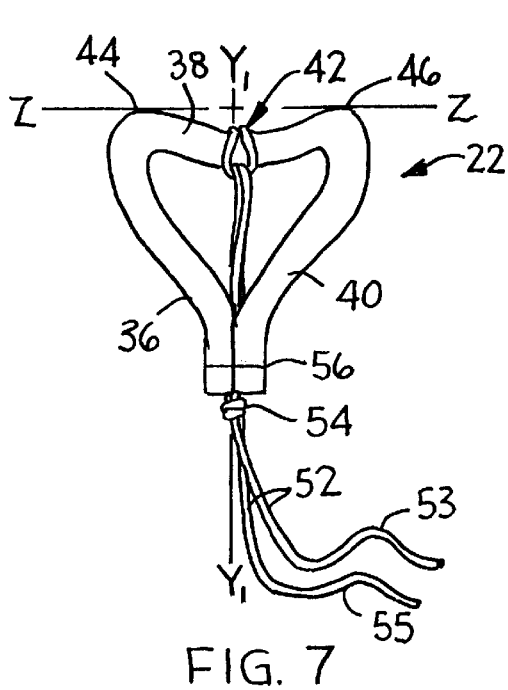
FIG. 7 is a side view of the softwind folded to form a generally M-shaped profile and showing the withdrawal string looped around the second portion.

Referring to FIG. 7, an alternative attachment method is depicted for securing the withdrawal string 52 to the second portion 38 of the softwind 22. In this figure, the withdrawal string 52 is merely looped upon itself and pulled taut. The free ends 53 and 55 of the withdrawal string 52 pass between the first and second ends, 24 and 26 respectively, of the softwind 22. However, the knot 54 is located away from the free ends 53 and 55 so that once the tampon is inserted into a woman's vagina, the second portion 38 can laterally expand outwardly until the knot 54 contacts the first and second ends, 24 and 26 respectively. When contact occurs, the second portion 38 of the softwind 22 will be stopped or restricted from laterally expanding outward to a greater extent. The knot 54 can be precisely located along the length of the withdrawal string 52 so as to control the amount the second portion 38 can actually expand. The knot 54 can be spaced from between about 1 inch to about 5 inches (about 2.5 mm to about 12.5 mm) from the free ends of the withdrawal string 52. The location of the knot 54 can be adjusted so as to control the amount the two lobes 44 and 46 can be spaced apart. This is an important feature for the knot 54 can be so located that it will prevent the second portion 38 from moving beyond the horizontal position, represented by a horizontal axis Z—Z. By so controlling the orientation of the second portion 38, one can be assured that both the cleft 42 and the trough 48 will be present when a downward force is exerted on the withdrawal string 52. When the withdrawal string 52 is pulled downward, the withdrawal string 52 will force the second portion 38 to move downward as well, along the vertical axis $Y_1$—$Y_1$, and draw the two lobes 44 and 46 inward toward one another. As the two lobes 44 and 46 move inward toward one another, the overall size and/or configuration of the tampon will become smaller and it can be comfortably removed.

It should be noted that the first and second ends, 24 and 26 respectively, can be held together by compressing the two ends adjacent to one another as is shown in FIG. 6. The compression step will be explained in more detail below. Alternatively, the first and second ends, 24 and 26 respectively, can be held securely together by a mechanical or chemical fastener 56, for example a thread, as is depicted in FIG. 7. Other attachment mechanisms can also be used, such as adhesive, one or more spots of glue, thermoplastic line, ultrasonics, etc. When the fastener 56 is a thread, it can be looped around the outer peripheries of the first and second ends, 24 and 26 respectively, or through the absorbent material.

Still, another way of holding the first and second ends, 24 and 26 respectively, together is to thread the withdrawal string 52 through the absorbent material so that the two ends 24 and 26 can not move apart from one another.

Figure 8:
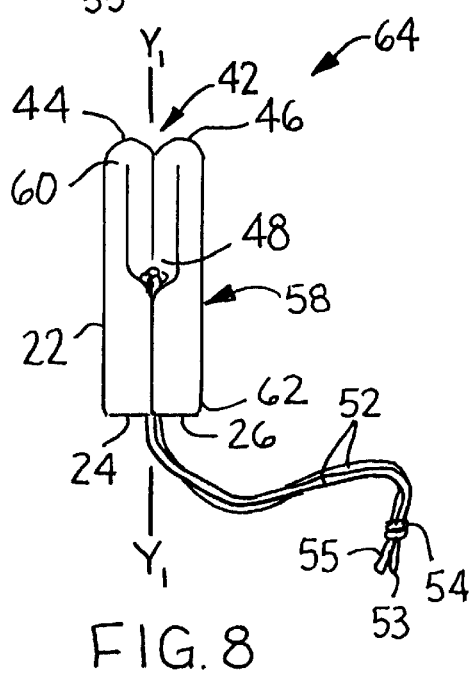
FIG. 8 is a side view of the softwind shown in FIG. 6 after it has been compressed into a pledget.

Referring now to FIG. 8, the softwind 22 is compressed into a pledget 58 after the withdrawal string 52 has been attached. The softwind 22 is compressed to a density of between about 0.1 grams per cubic centimeter (g/cc) to about 0.5 g/cc. Preferably, the softwind 22 is compressed to a density of from between about 0.15 g/cc to about 0.35 g/cc, and most preferably, the softwind 22 is compressed to a density of about 0.25 g/cc. The softwind 22 is also heated from between about 200° F. to about 300° F. (about 93.3° C. to about 148.9° C.) for a time period of from between about 15 seconds to about 60 seconds. Preferably, the heat set occurs at about 240° F. (about 115.6° C.) and the time period is about 45 seconds.

The pledget 58 has an insertion end 60 and an opposite, spaced apart trailing end 62. The compressed pledget 58 forms a finished tampon 64. Because the pledget 58 is formed from the softwind 22 after it has been configured into an M-shaped profile 34, the insertion end 60 will contain more absorbent material 10 than the trailing end 62. However, when the pledget 58 is compressed into a generally cylindrical-shape, it will have an essentially constant exterior periphery and therefore the diameter of the insertion end 60 will be approximately equal to the diameter of the trailing end 62. The cleft 42 which is present at the insertion end 60 of the pledget 58 will be visibly present as a crease since the first and second lobes 44 and 46 will be brought into contact with one another when the softwind 22 is compressed into the pledget 58.

It should be noted that the insertion end 60 contains a greater amount of absorbent material than the trailing end 62. Preferably, the insertion end 60 contains at least 1.25 times the amount of absorbent material 10 as does the trailing end 62. More preferably, the insertion end 60 will contain at least twice the amount of absorbent material 10 as the trailing end 62. This larger amount of absorbent material 10 at the insertion end 60 will cause the tampon 64 to asymmetrically expand during use such that the insertion end 60 will occupy a much larger area than the trailing end 62.

One will also notice that the M-shaped profile 34 allows the insertion end 60 to expand to a greater width dimension than thickness dimension. In this case, the width is shown as the distance between the first lobe 44 and the second lobe 46 while the thickness dimension goes into the paper, perpendicular to the vertical axis $Y_1$—$Y_1$. The reason for this is that the cross-section of a woman's vagina is not circular but instead is more rectangular in a relaxed state. More information on the geometry of a woman's vagina will be discussed below with reference to FIGS. 13–15.

Referring now to FIGS. 9 and 10, a tampon applicator 66 is shown having an arcuate or curved profile. The tampon applicator 66 includes an outer tube 68 and an inner tube 70. Preferably, both the outer tube 68 and the inner tube 70 are arcuate members formed on a radius and therefore each has an arcuate shape. It should be noted that the outer tube 68 has a radius "r" and the inner tube 70 has a radius "$r_1$", and the radius "r" can be equal to or different from the radius "$r_1$."

Both of the tubes 68 and 70 are hollow and each can be formed from similar or different materials. The materials can include paper, paperboard, cardboard, plastic, thermoplastic film, a combination thereof or any other type of suitable material. Preferably, both the outer tube 68 and the inner tube 70 are formed from the same material. The most common materials are paper, paperboard, cardboard and plastic. When paper or paperboard is used, it can be present as a single layer or as two or more layers. When two or more layers are used, they can be bonded together by an adhesive or glue to form a laminate structure. The outside surface of the outer tube 68 can also be coated with a wax or water-insoluble polymer to render it water-resistant.

Suitable plastic materials include polyolefins such as low density polyethylene and polypropylene. The outer tube 68 should have sufficient strength and rigidity to prevent collapsing under normal vaginal pressures. The outer tube 68 can be formed into a cylindrical shape having a longitudinal seam or be spirally or convolutely wound. The outer tube 68 has a relatively small diameter of from between about 10 mm to about 20 mm. The particular diameter of the outer tube 68 will depend upon the size of the tampon which is to be held therein. For example, a "junior" or "regular" size tampon will require a smaller diameter tube than would a "super" or a "super-plus" size tampon.

The inner tube 70 is slightly smaller in diameter than the outer tube 68 and is designed to telescopically slide within the inner diameter of the outer tube 68. Preferably, the inner tube 70 is made from the same material as the outer tube 68. It should be noted that the curved tampon applicator 66 could be constructed according to the teachings of Paul et al., U.S. Pat. No. 5,158,535 which is assigned to Kimberly-Clark Corporation. This patent is incorporated by reference and made a part hereof.

The tampon applicator 66 also contains an insertion tip 72 which is formed on one end of the outer tube 68 and contains a plurality of soft and flexible petals 74. The petals 74 can be arranged to form a dome-shaped nose. The petals 74 are separated by narrow slots 76. The slots 76 allow each petal 74 to radially flex or bend outward so as to provide an enlarged opening through which the tampon 64 can exit when it is pushed forward by the inner tube 70. Either an even or an odd number of petals 74 can be used, but preferably, there are an odd number of petals 74, such as 3, 5, 7, etc. By using an odd number of petals 74, one can prevent the outer tube 68 from collapsing or flattening after the tampon 64 has been expelled. Most preferably, the tampon applicator 66 will contain five petals 74. By preventing the outer tube 68 from collapsing, one can be assured that the vaginal tissue will not be pinched when the tampon applicator 66 is inserted or removed from the user's vagina. For optimum performance, all of the petals 74 should have approximately the same shape and dimension. Each of the petals 74 can have an elongated, approximately truncated shape, with a rounded end and each can have a length of about 7/16 of an inch (about 11.1 mm).

The tampon applicator 66 can also contain a fingergrip 78 formed on the opposite end of the outer tube 68. The fingergrip 78 can contain one or more ridges 80 which will prevent the user's fingers from slipping as she holds the tampon applicator 66. The fingergrip 78 can also contain flattened surfaces such as shown in U.S. Pat. No. 5,158,535, which issued to Paul et al. and is assigned to Kimberly-Clark Corporation. The flattened surfaces are aligned perpendicular to the radius of curvature of the tampon applicator 66 such that it facilitates orientation of the applicator 66 into a woman's vagina.

It should also be noted that the tampon 64 will be oriented within the arcuately-shaped tampon applicator 66 such that the cleft 42 is aligned parallel with the radius "r" of the outer tube 68. That is, the cleft 42 is aligned perpendicular to the arcuately shaped centerline A—A shown FIG. 9. Another way of stating this is to say that in FIG. 10, the cleft 42 is aligned parallel to the arcuately-shaped centerline A—A since FIG. 10 is rotated 90° relative to FIG. 9. This alignment is important, for it will assure that the tampon 64 is correctly oriented within a woman's vagina after it is expelled from the tampon applicator 66.

Figure 11:
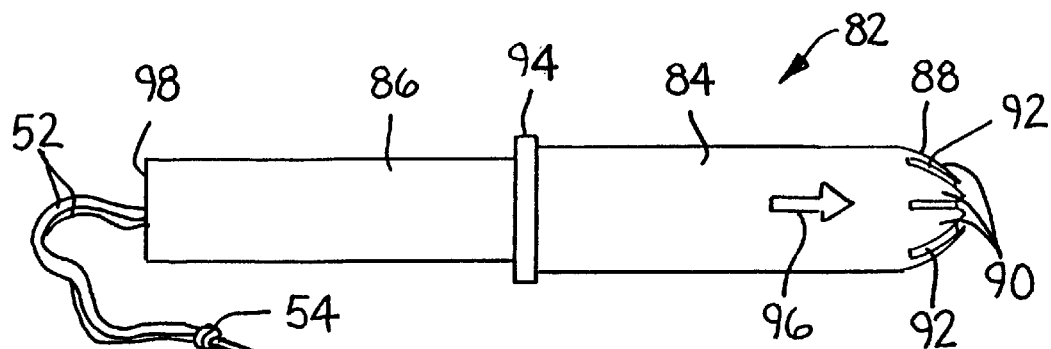
FIG. 11 is a side view of a two piece tampon applicator having an inner tube and an outer tube.
Figure 12:
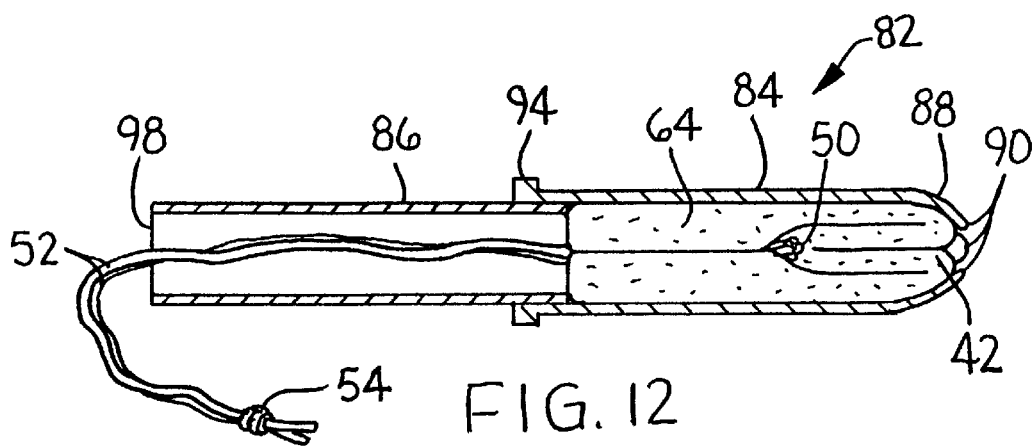
FIG. 12 is a cross-sectional view of the tampon applicator shown in FIG. 11 depicting the tampon being retained in the outer tube prior to insertion into a woman's vagina.

Referring now to FIGS. 11 and 12, a straight tampon applicator 82 is shown which is comprised of a hollow outer tube 84 and a hollow inner tube 86. The outer tube 84 is designed to house a tampon 64 while the inner tube 86 is telescopically slidable within the inner periphery of the outer tube 84 so as to expel the tampon 64 therefrom. The outer tube 84 has an insertion tip 88 which contains a plurality of petals 90 formed thereon. The petals 90 are separated by narrow slits or slots 92. The petals 90 and slots 92 serve the same function as the petals 74 and the slots 76 explained above in reference to FIGS. 9 and 10. The straight tampon applicator 82 also contains a fingergrip 94 in the form of a flange integrally formed on the opposite end of the outer tube 84. Since the straight tampon applicator 82 does not contain a curvature with which it can be oriented relative to a woman's vagina, it should contain some type of indicator 96 so as to aid the user in correctly orienting the tampon 64 relative to her vagina. The indicator 96 can be an arrow, a longitudinal line or some other type of marking which is painted, printed, embossed, applied or formed on the outer surface of the outer tube 84. For example, in FIG. 11, the indicator 96 is shown as an elongated arrow positioned adjacent to the insertion end 88. The tampon 64 should be inserted into the applicator 82 and oriented such that the cleft 42 is aligned parallel to the indicator 96.

It should also be noted that the inner tube 86 has a trailing end 98 which is spaced away from the fingergrip ring 92 when a tampon 62 is housed in the outer tube 84. As the inner tube 84 is pushed into the outer tube 84 to expel the tampon 62 therefrom, the trailing end 98 of the inner tube 86 will approach the fingergrip ring 94.

Figure 13:
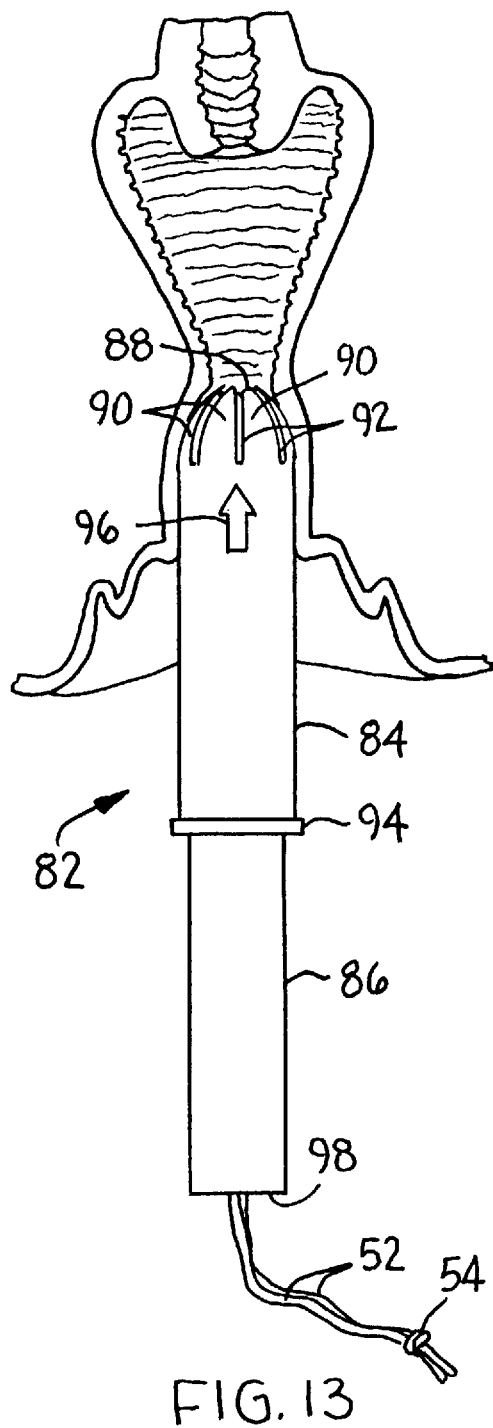
FIG. 13 is a front sectional view of a portion of the pelvic area of the female body taken in a plane through the cervix and introitus and showing the position of the tampon applicator immediately prior to expelling the tampon into the vagina.
Figure 14:
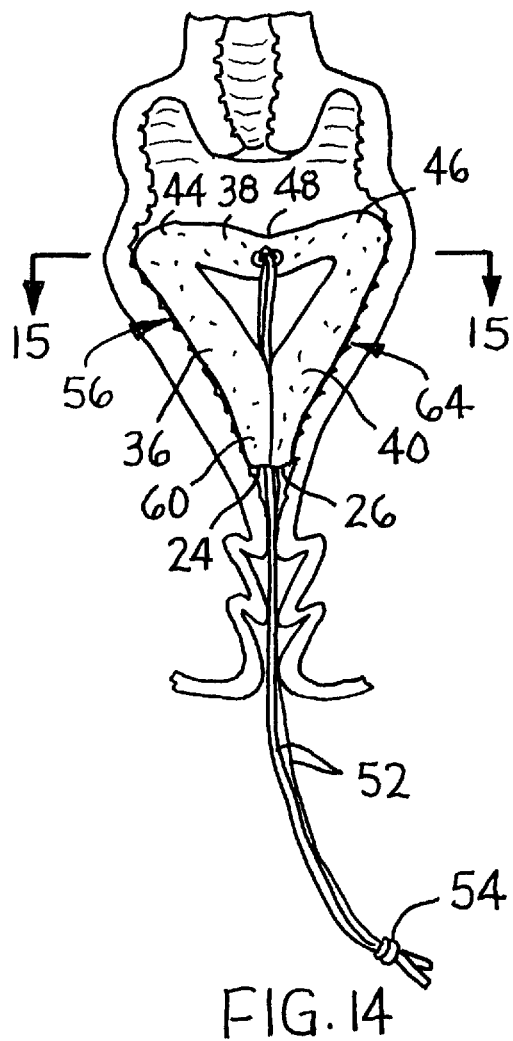
FIG. 14 is a view similar to that depicted in FIG. 13 showing the tampon after placement in the vagina and after the tampon applicator has been withdrawn.
Figure 15:
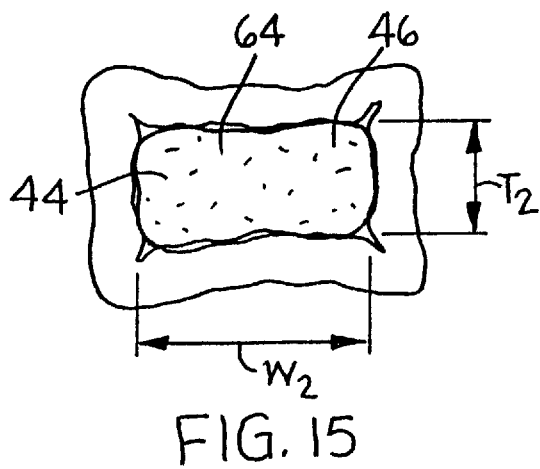
FIG. 15 is a vertical, lateral sectional view of the female vagina taken along line 15—15 of FIG. 14 illustrating how the tampon fills the cross-sectional area of the vagina.

Referring to FIGS. 13–15, the insertion and positioning of the tampon 64 within a woman's vagina will be described. In FIG. 13, the straight tampon applicator 82 housing the tampon 64 is held by the user between her thumb and middle fingers. The thumb and middle fingers will contact the outer tube 84 just ahead of the fingergrip 94 while her index finger will rest on the trailing end 98 of the inner tube 86. The outer tube 84 is inserted through the introitus, until the insertion tip 88 is approximately in the lower end of the vagina. As the tampon applicator 82 is inserted, the indicator 96 should be aligned so that it is facing and parallel to the woman's belly button.

Once the outer tube 84 has been positioned such that the insertion tip 88 is adjacent to the lower end of the vagina, the user will push the inner tube 86 into the outer tube 84 with her index finger. As this occurs, the petals 90 will expand radially outward and allow the tampon 64 to be expelled into the vaginal cavity.

Referring to FIGS. 14 and 15, the orientation of the tampon 64 within the vaginal cavity is depicted. In FIG. 14, the tampon 64 is shown expanded laterally so that it occupies the opening of the vagina. In FIG. 15, the tampon 64 is shown having a width $W_2$ and a thickness $T_2$. The width $W_2$ is greater than the thickness $T_2$. Because of the unique shape of the vaginal cavity, in order to effectively prevent the leakage of body fluid from the vagina, a tampon must have a width $W_2$ to thickness $T_2$ ratio of greater than 1. Preferably, the width $W_2$ to thickness $T_2$ ratio is about 2:1.

The tampon 64 laterally expands to an open position, as that shown in FIG. 14, after being inserted into the vagina.

The ability of the tampon 64 to expand to occupy the vagina cavity results from a number of phenomena, one being the natural resiliency of the compacted fibers within the tampon 64. A second factor is the folds 28, 30 and 32 which provide the absorbent 10 with a natural tendency to return to their non-compressed, generally M-shaped profile 34. A third phenomenon is that the liquid-permeable cover 16 which is folded along with the absorbent 10 is aligned adjacent to itself in the area of the cleft 42. Since the cover 16 does not want to bond or adhere to itself, it has a natural tendency to separate and spread the absorbent 10 apart once the forces retaining the pledget 58 in a generally cylindrical shape are removed. In other words, once the pledget 58 is expelled from the outer tube 84, the absorbent 10 and cover 16 are free to expand outward to the generally M-shaped profile 34. The expansion of the second portion 38 of the tampon 64 allows a bridge to be formed across the vaginal cavity immediately below the cervix. This bridging effect causes the lobes 44 and 46 to move laterally outward and contact the inner walls of the vagina. This action essentially blocks the vaginal cavity and prevents the leakage of body fluid out of the vagina. This gives the tampon 64 an expanded configuration which best approximates the profile of the vagina, as shown in FIG. 13. While this is occurring, the trailing end 62 of the pledget 58 will stay together and expand to a much less extent in the width and thickness directions. This inability to appreciably expand is the result of the fastener 56.

Figure 16:
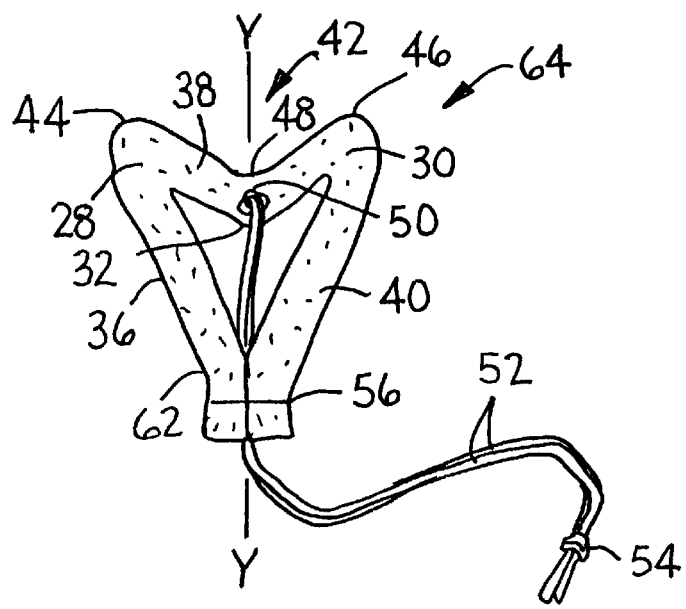
FIG. 16 is a side view showing one configuration of the tampon after removal from a woman's vagina.

Referring now to FIG. 16, the general shape of the tampon 64 is shown as it is ready to be removed from the vaginal cavity. One will notice that the general M-shaped profile 34 will become more pronounced as a downward force is exerted on the withdrawal string 52. As one continues to pull downward on the withdrawal string 52, the lobes 44 and 46 will move closer together because of the force exerted at the third fold 32. As the withdrawal string 52 is pulled downward, the trailing end 62 of the pledget 58 will be forced out of the vagina. The inner walls of the introital region will cause the lobes 42 and 44 to be pressed together as they exit the introital region. This particular M-shaped profile 34 permits for an easy and comfortable withdrawal of the tampon 64 from a woman's vagina.

METHOD

Figure 17:
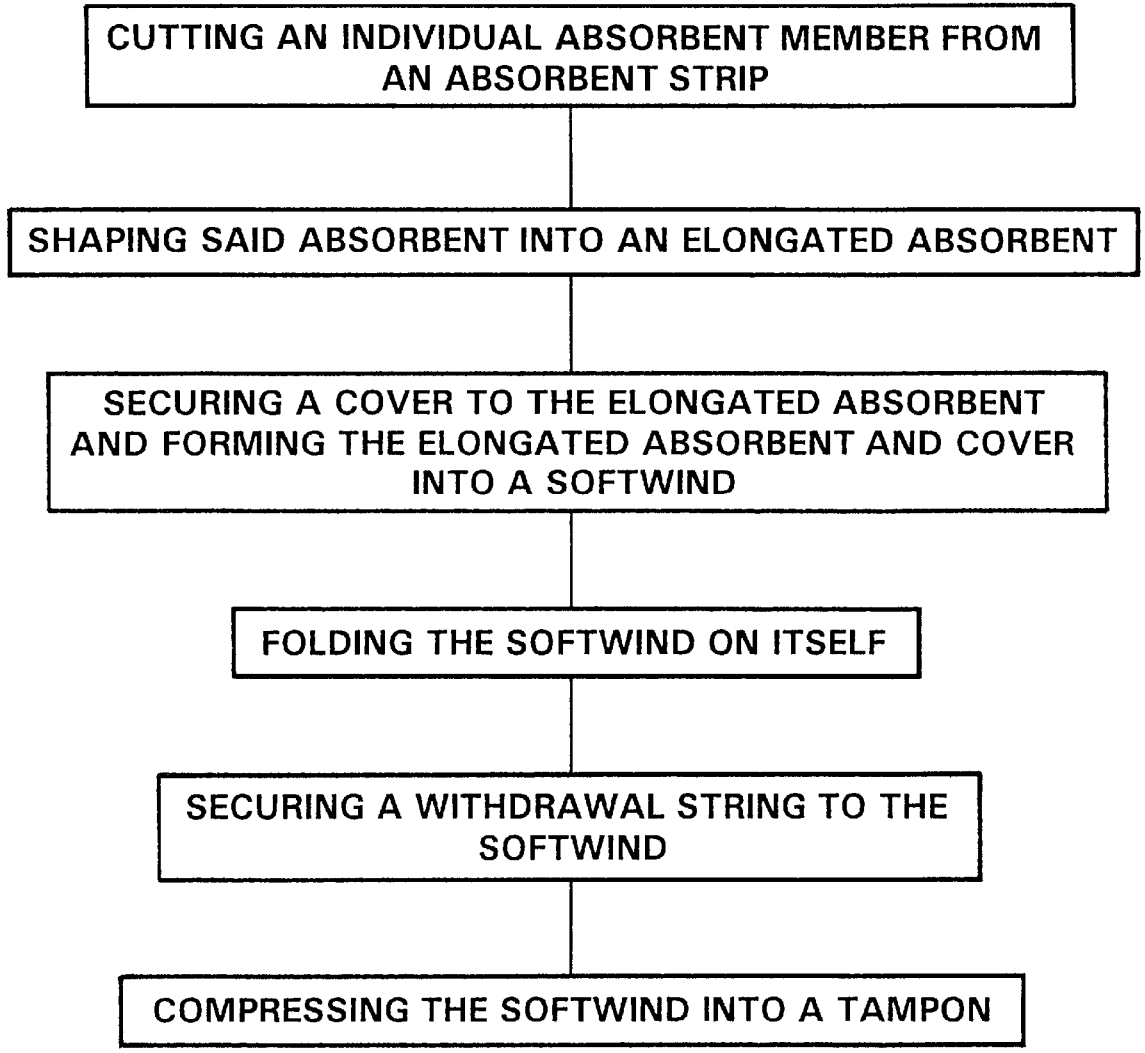
FIG. 17 is a flow diagram of a method of forming a tampon which can be comfortably withdrawn from a body cavity.

The method of forming the catamenial tampon 64 will now be explained with reference to the structure shown in FIGS. 1–16 and to the flow diagrams shown in FIGS. 17–19. The method includes cutting an individual absorbent member 12 from an absorbent strip 10. Each absorbent member 12 has a central longitudinal axis X—X and a central transverse axis Y—Y. The absorbent member 12 is then rolled, folded or somehow shaped to form an elongated absorbent 14 having an outer periphery 15. The absorbent member 12 can be shaped such as by rolling along the central transverse axis Y—Y, by folding the absorbent member 12 on its side, by a combination of folding and/or rolling the absorbent member 12, or somehow shaping the absorbent member 12 to form the elongated absorbent 14.

A liquid-permeable cover 16 is then secured to the outer periphery 15 of the elongated absorbent 14 to form a softwind 22. One way of securing the cover 16 to the elongated absorbent 14 is to place the elongated absorbent 14 on the liquid-permeable cover 16 and then roll both the elongated absorbent 14 and the cover 16 together to form the softwind 22. A depiction of this particular example is shown in FIG. 4. The liquid-permeable cover 16 can then be bonded to itself or to the absorbent 14.

The softwind 22 has a first end 24 and a second end 26. The two ends, 24 and 26 respectively, are spaced apart and separated by a distance $L_2$, see FIG. 5, when the softwind 22 is in a non-folded condition. The softwind 22 is then folded on itself such that the first and second ends, 24 and 26 respectively, abut one another or are aligned adjacent to one another. The softwind 22 should be folded such that it contains at least two folds 28 and 30, and preferably, three folds 28, 30 and 32. The folding of the softwind 22 gives it a generally M-shaped profile 34. By folding the softwind 22 upon itself at two, and preferably three locations, a first portion 36, a second portion 38, and a third portion 40 are formed. The first, second, and third portions, 36, 38, and 40 respectively, can all be of the same length or of different lengths. Alternatively, the second portion 38 which bridges the first portion 36 and the third portion 40 can be shorter in length than the first portion 36 and/or shorter in length than the third portion 40.

It should be noted that the second portion 38 is integrally connected to both the first portion 36 and to the third portion 40. Since the first and third portions, 36 and 40 respectively, establish the overall length of the pledget 58 which is formed once the softwind 22 is compressed, it is advantageous to make both of them of the same length. When the softwind 22 is folded at least two times, the first and second ends, 24 and 26 respectively, can be aligned adjacent to one another so that they abut and terminate in the same plane. In other words, the outer surface of the first and second ends, 24 and 26 respectively, will be flush with one another. It should be mentioned that some tampon manufacturers may wish to vertically offset the first and second ends, 24 and 26 respectively, and this can be accomplished without deviating from the spirit and scope of the present invention.

When starting with a softwind 22 having a length of approximately 6 inches (about 152 mm), it is advantageous to fold the softwind 22 at two locations 28 and 30. The two folds 28 and 30 are located between the first and second ends, 24 and 26 respectively, such that the second portion 36 will have a length of at least about 2 inches (51 mm). When one starts with a softwind 22 greater than 6 inches (152 mm) in length, it is still advantageous to construct the second portion 38 such that it has a length of at least about 2 inches. In this case, the first and third portions, 36 and 40 respectively, can be slightly longer in length than 2 inches (51 mm).

As mentioned above, by folding the softwind 22 at three locations, 28, 30, and 32 respectively, all of which are located between the first and second ends, 24 and 26 respectively, the generally M-shaped profile 34 is readily obtained. In the M-shaped profile 34, a cleft 42 is established having a length or depth $L_3$, see FIG. 6. The length $L_3$ is the vertical distance measured from a horizontal line passing through the tips of the lobes 44 and 46 and a horizontal line passing tangentially through the bottom surface of the trough 48. This length $L_3$ will represent from between about 5% to about 80% of the length $L_4$ of the generally M-shaped profile 34.

The method also includes securing a withdrawal string 52 to the second portion 38 of the softwind 22. In this method, once the generally M-shaped profile 34 is formed, the withdrawal string 52 is secured to the softwind 22 approximate the middle of the second portion 38. The withdrawal string 52 is secured to the second portion 38 by looping the withdrawal string 52 around the second portion 38 and then passing the withdrawal string 52 onto itself to form a cinch which can be tightened. The free ends 53 and 55 of the withdrawal string 52 can then be positioned between the first and third portions 36 and 40 of the softwind 22 as it is compressed into the pledget 58.

The method further includes compressing the softwind 22, which has been folded into the generally M-shaped profile 34, into a cylindrically shaped pledget 58. The cylindrically shaped pledget 58 has an insertion end 60 and a trailing end 62. The insertion end 60 is located adjacent to the second portion 38. Because of the M-shaped profile of the softwind 22 before it is compressed, the insertion end 60 will contain more absorbent than the trailing end 62. This occurs because as the softwind 22 is folded, all of the absorbent material present in the second portion 38 will be present at the insertion end 60. After the pledget 58 has been formed the tampon 64 is complete. The tampon 64 is unique in that the insertion end 60 is capable of collapsing upon itself as pressure is exerted on the withdrawal string 52 to provide a comfortable removal from the body cavity. The withdrawal string 52 will facilitate comfortable removal of the tampon 64 from a woman's vagina after the tampon 64 has accomplished its intended purpose. That is, after the tampon 64 has absorbed menstrual fluid, blood, menses and/or other body fluids normally discharged by a woman's vagina.

Figure 18:
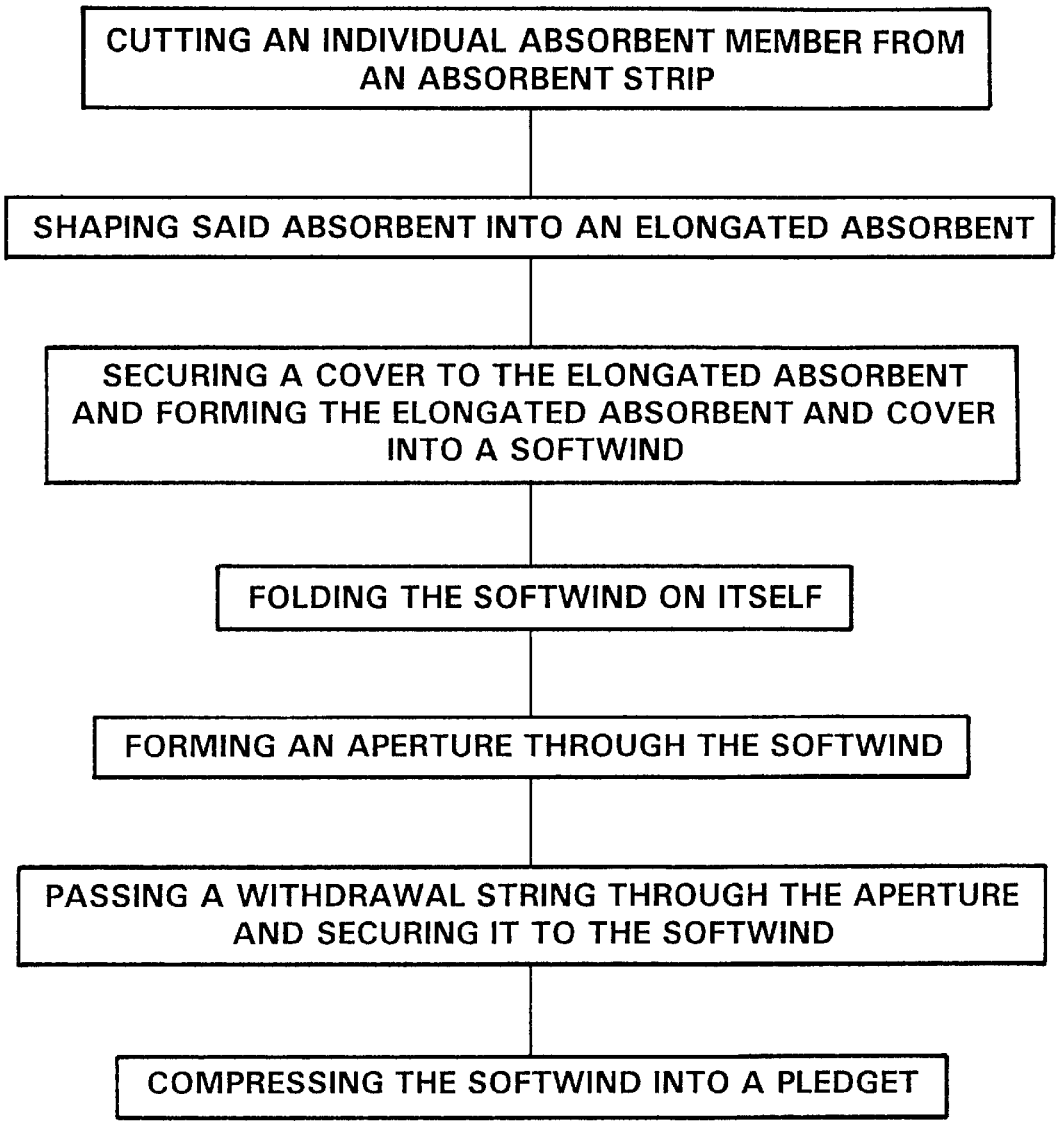
FIG. 18 is a flow diagram of an alternative method of forming a tampon which can be comfortably withdrawn from a body cavity.

Referring to FIG. 18, an alternative method of attaching the withdrawal string 52 to the softwind 22 is depicted. In this method, an aperture 50 is formed through the second portion 38 approximate the location of the cleft 42. The aperture 50 should be formed approximately half way between the folds 28 and 30. Or stated another way, the aperture 50 should be formed at the location of the fold 32. The aperture 50 should be formed such that it is perpendicularly aligned with the vertical axis $Y_1$—$Y_1$. The aperture 50 can be formed at a slight angle if desired. One means of forming the aperture 50 is to insert a needle through the softwind 22 such that upon removal of the needle, the aperture 50 is formed. The aperture 50 will pass completely through the thickness of the second portion 38 of the softwind 22. Other methods of forming the aperture 50 can also be used and these methods are known to those skilled in the art. The withdrawal string 52 is then passed through the aperture 50 and looped upon itself so as to make it tight or taut to the second portion 38.

Figure 19:
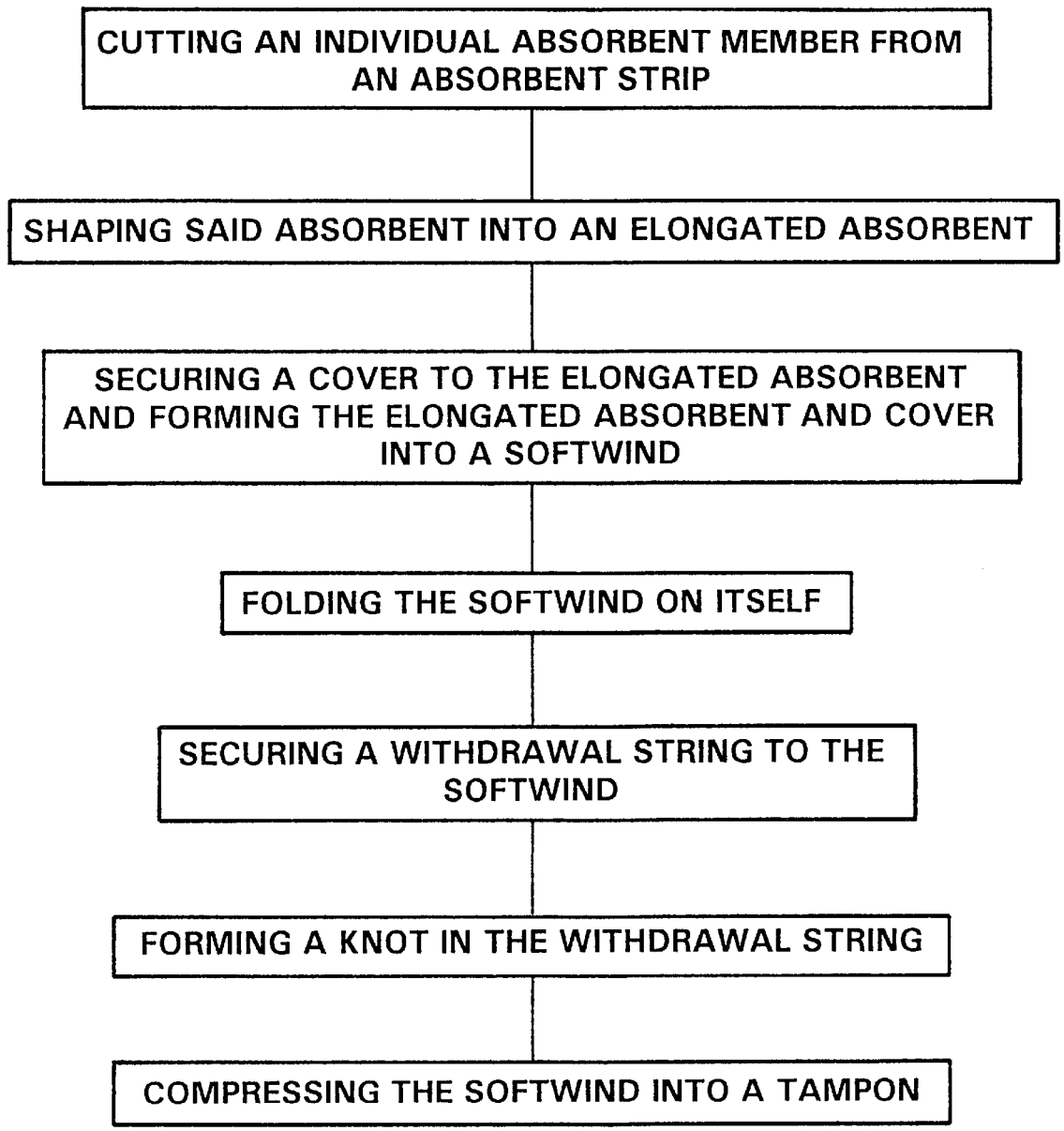
FIG. 19 is a flow diagram of still another method of forming a tampon which can be comfortably withdrawn from a body cavity.

Referring to FIG. 19, still another method is depicted for forming the tampon 64. In this method, the withdrawal string 52 is secured to the second portion 38 of the softwind 22 and then the two free ends 53 and 55 are tied together to form a knot 54. The knot 54 will prevent the withdrawal string 52 from separating from the softwind 22. The knot 54 can be formed adjacent to the free ends, 53 and 55 respectively, or it can be formed at a location away from the free ends, 53 and 55 respectively. The knot 54 can be positioned such that it will abut the trailing end 62 of the pledget 58 and thereby limit the amount the second portion 38 can laterally expand outward while within the woman's vagina. By limiting the amount the second portion 38 can expand, one can be assured that the cleft 42 will always be present and that at the time of withdrawal, the insertion end 60 will collapse upon itself as downward pressure is exerted on the withdrawal string 52.

It is also advantageous that upon removal of the tampon 64 from the body cavity that the first and third portions, 36 and 40 respectively, be held together approximate the trailing end 62. By keeping the first and second ends, 24 and 26 respectively, in close contact, one can minimize the overall size or diameter of the trailing end 62. A smaller size or diameter will facilitate an easier and more comfortable withdrawal of the tampon 64. One way to assure that the first and third portion, 36 and 40 respectively, stay together is to secure them by a fastener 56. The fastener 56 can be a piece of thread which is looped around the two portions 36 and 40 or is passed through the two portions 36 and 40 to keep them together. Other types and kinds of fasteners can be used in place of the thread 56. Mechanical fasteners known to those skilled in the art as well as chemical fasteners can be utilized. Some examples include thermoplastic line, adhesive, glue, ultrasonic bonding and the like.

After the tampon 64 is formed, it can be positioned in a tampon applicator 66 or 82. The tampon applicator can be an arcuately-shaped applicator 66, as shown in FIGS. 9 and 10, or it can be a straight applicator 82, as shown in FIGS. 11 and 12. When the tampon 66 is positioned into the outer tube 68 of an arcuately-shaped tampon applicator 66, the cleft 42 has to be aligned parallel to the radius which forms the arcuately-shaped outer tube 68. This will assure that the tampon 64 is properly positioned within a woman's vagina after being expelled from the applicator 66. Likewise, when the tampon 64 is to be positioned in the outer tube 84 of a straight tampon applicator 82, the cleft 42 should be aligned parallel to the indicator 96. This will assure that the tampon 64 is properly positioned within a woman's vagina after being expelled from the applicator 82.

Lastly, the generally M-shaped profile 34 of the tampon 64 enables the insertion end 60 to contain more absorbent material than the trailing end 62. This additional absorbent material at the insertion end 60 is advantageous in intercepting fluid flow and preventing premature leakage of body fluid past the tampon 64. The generally M-shaped profile 34 also has the ability to expand to occupy the entire cross-sectional opening of the woman's vagina during use, and therefore is capable of preventing body fluid from leaking past the tampon 64.

While the invention has been described in conjunction with several specific embodiments, it is to be understood that many alternatives, modifications and variations will be apparent to those skilled in the art in light of the aforegoing description. Accordingly, this invention is intended to embrace all such alternatives, modifications and variations which fall within the spirit and scope of the appended claims.

I claim:

1. A method of forming a tampon, said method comprising the steps of:

a) cutting an individual absorbent member from an absorbent strip;

b) shaping said absorbent member by rolling or folding into an elongated absorbent having an outer periphery;

c) securing a liquid-permeable cover to said outer periphery of said elongated absorbent to form a softwind, said softwind having a first end and a second end;

d) providing an M-shaped profile by folding said softwind on itself such that said first and second ends are aligned adjacent to one another and such that said softwind contains three folds between said first and second ends, said folds dividing said softwind into first, second and third portions to form an M-shaped profile having a first lobe, a second lobe, and a second portion cleft between said first lobe and said second lobe;

e) securing a withdrawal string to said second portion cleft between said first lobe and said second lobe; and f) compressing said softwind into a cylindrically shaped pledget having an insertion end, a trailing end, and a substantially constant exterior periphery, said insertion end containing more absorbent material than said trailing end, said pledget and attached withdrawal string forming a tampon wherein said insertion end is capable of collapsing upon itself during end use as pressure is exerted on said withdrawal string to provide a comfortable removal from a body cavity.

2. The method of claim 1 further comprising forming an aperture through said second portion cleft between said first lobe and said second lobe and passing said withdrawal string through said aperture.

3. The method of claim 2 further comprising looping said withdrawal string upon itself after said withdrawal string has passed through said aperture.

4. The method of claim 1 wherein a portion of said withdrawal string is positioned between said first and third portions as said softwind is compressed into said pledget.

5. The method of claim 1 wherein said withdrawal string contains two free ends and said method further comprises forming a knot adjacent to said free ends.

6. The method of claim 5 further comprising forming a knot in said withdrawal string at a location away from said free ends, said knot capable of abutting said trailing end of said pledget and limiting the amount said second portion cleft between said first lobe and said second lobe can laterally expand outward.

7. The method of claim 1 further comprising securing said first and third portions together approximate said trailing end of said pledget.

8. The method of claim 7 wherein said first and third portions are secured together by a thread.

9. The method of claim 1 wherein said second portion cleft has a depth smaller than the length of said first or third portions.

10. A method of forming a tampon, said method comprising the steps of:
   a) cutting an individual absorbent member from an absorbent strip;
   b) shaping said absorbent member by rolling or folding into an elongated absorbent having an outer periphery;
   c) securing a liquid-permeable cover to said outer periphery of said elongated absorbent to form a softwind, said softwind having a first end and a second end;
   d) providing an M-shaped profile by folding said softwind on itself such that said first and second ends are aligned adjacent to one another and said softwind contains three folds between said first and second ends, said folds dividing said softwind into first, second and third portions to form an M-shaped profile having a first lobe, a second lobe, and a second portion cleft between said first lobe and said second lobe;
   e) forming an aperture through said second portion cleft between said first lobe and said second lobe of said softwind;
   f) passing a withdrawal string through said aperture and looping said withdrawal string upon itself to hold it secure to said softwind; and
   g) compressing said softwind into a cylindrically shaped pledget having an insertion end formed by said first lobe and said second lobe and a trailing end, said insertion end located forward to said second portion cleft between said first lobe and said second lobe, said compressed pledget and attached withdrawal string forming a tampon wherein said insertion end is capable of collapsing upon itself during end use as pressure is exerted on said withdrawal string to provide a comfortable removal from a body cavity.

11. The method of claim 10 wherein a portion of said withdrawal string is positioned between said first and second portions as said softwind is compressed into said pledget.

12. The method of claim 10 wherein said withdrawal string contains two free ends and said method further comprises forming a knot adjacent to said free ends.

13. The method of claim 12 further comprising forming a knot in said withdrawal string at a location away from said free ends by a distance of about one to five inches, said knot capable of abutting said trailing end of said pledget and limiting the amount said second portion cleft between said first lobe and said second lobe can laterally expand outward.

14. The method of claim 10 further comprising securing said first and third portions together approximate said trailing end of said pledget.

15. The method of claim 14 wherein said first and third portions are secured together by a thread.

16. A method of forming a tampon, said method comprising the steps of:
   a) cutting an individual absorbent member from an absorbent strip;
   b) shaping said absorbent member by rolling or folding into an elongated absorbent having an outer periphery;
   c) securing a liquid-permeable cover to said outer periphery of said elongated absorbent to form a softwind, said softwind having a first end and a second end;
   d) providing an M-shaped profile by folding said softwind on itself such that said first and second ends are aligned adjacent to one another and said softwind contains three folds between said first and second ends, said folds dividing said softwind into first, second and third portions to form an M-shaped profile having a first lobe, a second lobe, and a second portion cleft between said first lobe and said second lobe, wherein said second portion cleft has a depth of 5% to 80% of the length of said M-shaped profile;
   e) securing a withdrawal string to said second portion cleft between said first lobe and said second lobe;
   f) forming a knot in said withdrawal string at a position along the length of said withdrawal string to control the amount said second portion can expand within a user's vagina to prevent the second portion from losing a trough shape within a user's vagina; and
   g) compressing said softwind into a cylindrically shaped pledget having an insertion end formed by said first lobe and said second lobe and a trailing end, said insertion end located forward to said second portion cleft between said first lobe and said second lobe, said compressed pledget and attached withdrawal string forming a tampon wherein said insertion end is capable of collapsing upon itself during end use as pressure is exerted on said withdrawal string to provide a comfortable removal from a body cavity.

17. The method of claim 16 wherein said withdrawal string contains two free ends and said knot is formed at a distance away from said free ends.

18. The method of claim 16 wherein said withdrawal string contains two free ends and said knot is formed at a distance of about one to five inches away from said free ends.

19. The method of claim 16 further comprising securing said first and third portions together approximate said trailing end of said pledget.

20. The method of claim 19 wherein said first and third portions are secured together by a thread.

* * * * *